(12) United States Patent
Albes

(10) Patent No.: US 11,369,472 B2
(45) Date of Patent: Jun. 28, 2022

(54) HEART VALVE IMPLANT AND HEART VALVE IMPLANT SYSTEM

(71) Applicant: IMMANUEL ALBERTINEN DIAKONIE GGMBH, Hamburg (DE)

(72) Inventor: Johannes Albes, Berlin (DE)

(73) Assignee: IMMANUEL ALBERTINEN DIAKONIE GGMBH, Berlin (DE)

( * ) Notice: Subject to any disclaimer, the term of this patent is extended or adjusted under 35 U.S.C. 154(b) by 278 days.

(21) Appl. No.: 16/498,988

(22) PCT Filed: Mar. 28, 2018

(86) PCT No.: PCT/EP2018/058028
§ 371 (c)(1),
(2) Date: Jan. 13, 2020

(87) PCT Pub. No.: WO2018/178210
PCT Pub. Date: Oct. 4, 2018

(65) Prior Publication Data
US 2020/0383784 A1 Dec. 10, 2020

(30) Foreign Application Priority Data
Mar. 28, 2017 (DE) .................. 10 2017 002 974.1

(51) Int. Cl.
*A61F 2/24* (2006.01)
(52) U.S. Cl.
CPC .......... *A61F 2/2466* (2013.01); *A61F 2/2454* (2013.01)

(58) Field of Classification Search
CPC .... A61F 2/2442; A61F 2/2454; A61F 2/2457; A61F 2/246; A61F 2/2463; A61F 2/2466
See application file for complete search history.

(56) References Cited

U.S. PATENT DOCUMENTS

| | | |
|---|---|---|
| 3,608,554 A | 9/1971 | McGuinness et al. |
| 8,216,302 B2 | 7/2012 | Wilson et al. |
| 8,480,730 B2 | 7/2013 | Maurer et al. |
| 8,758,393 B2 | 6/2014 | Zentgraf |
| 8,888,844 B2 | 11/2014 | Eliasen et al. |

(Continued)

FOREIGN PATENT DOCUMENTS

| | | |
|---|---|---|
| DE | 2060814 A1 | 6/1971 |
| WO | 06078694 A2 | 7/2006 |
| WO | 15020971 A1 | 2/2015 |

OTHER PUBLICATIONS

International Search Report for WO2018EP58028 dated Jun. 18, 2018 (pp. 1-4).

*Primary Examiner* — William H Matthews
(74) *Attorney, Agent, or Firm* — Millen White Zelano and Branigan, PC; Csaba Henter

(57) ABSTRACT

A heart-valve implant, in particular for mitral-valve reconstruction, which is to be carried out on a beating heart with a minimally-invasive method where access to the heart is made between the $3^{rd}$ or $4^{th}$ intercostal space in the right area of the thorax, where via this access path, the heart-valve implant is inserted into the left ventricle of the heart, which heart-valve implant includes a fastener for picking up a valve leaflet, an anchor for fastening the fastener in the myocardium, and a connector, which connects the anchor to the fastener.

22 Claims, 8 Drawing Sheets

(56) References Cited

U.S. PATENT DOCUMENTS

| | | |
|---|---|---|
| 8,894,705 B2 | 11/2014 | Eliasen et al. |
| 9,044,221 B2 | 6/2015 | Zentgraf et al. |
| 9,192,374 B2 | 11/2015 | Zentgraf |
| 9,232,999 B2 | 1/2016 | Maurer et al. |
| 9,700,300 B2 | 7/2017 | Speziali |
| 10,449,046 B2 | 10/2019 | Rafiee |
| 2007/0150000 A1 | 6/2007 | Osypka |
| 2010/0161041 A1 | 6/2010 | Maisano et al. |
| 2010/0179574 A1* | 7/2010 | Longoria ............ A61F 2/2463 606/151 |
| 2011/0011917 A1* | 1/2011 | Loulmet ............ A61B 17/0401 227/181.1 |
| 2014/0067048 A1 | 3/2014 | Chau et al. |
| 2015/0073547 A1 | 3/2015 | Eliasen et al. |
| 2018/0243087 A1* | 8/2018 | Kapadia ............ A61F 2/2466 |
| 2018/0289473 A1* | 10/2018 | Rajagopal ............ A61F 2/2427 |

\* cited by examiner

HEART VALVE IMPLANT AND HEART VALVE IMPLANT SYSTEM

This invention relates to a heart-valve implant and a heart-valve implant, in particular for minimally-invasive heart surgery.

BACKGROUND

In the heart-surgery field, instruments, devices or methods are used in order to examine the interior of living organisms, for example the interior of the heart, and/or to use surgical procedures, for example the minimally-invasive repair of heart valves, whereby surgical instruments are used that, with access to the heart, allow various repairs and the insertion of implants into beating hearts to be performed.

Today, various conventional and minimally-invasive surgical methods are used in heart-valve procedures. Heart-valve procedures are catheter-supported or surgical procedures on heart valves or heart-valve leaflets, with the purpose of restoring the functionality of a heart valve. For restoring functionality, various technical methods and surgical instruments are available. Such techniques comprise the repair and the replacement of heart valves. In order to be able to conduct a repair on the heart, there are various access paths. A surgical access path to the heart is carried out by, for example, the thoracotomy in the form of a median sternotomy, which enables access in the patient's chest cavity. To this end, the sternum must be cut open or sawed open according to the length, and with a rib spreader, the two halves of the ribcage are then stretched from one another. The surgical team now gains a clear view of the heart and the vascular systems of the thorax. Because of the good visualization and size of the operating field, a large number of surgical instruments can be used. In a patient, such an opening of the ribcage, however, causes a high degree of traumatization, extended stays in the hospital and an extended healing process. This known access method and the surgical instruments that are used in this respect are only shown here in order to document the state of the art, but they are not to be further considered.

In the case of many heart diseases or in the case of cardiac insufficiencies, the procedure on the heart is performed using catheters. Many heart-valve defects can be corrected in a gentle way by modern catheter methods, and more major operations can occasionally be avoided. In particular, in this day and age, defects of the heart valves of the left half of the heart, i.e., of the aortic valve and mitral valve, are treated using a catheter. As also in the case of other catheter interventions, a plastic catheter is advanced via a blood vessel into the groin or into the arm up to the heart. Also, this access method (transcatheter technology) to the heart is not to be considered here in more detail.

For a large number of heart diseases or cardiac insufficiencies, access to the heart is gained using minimally-invasive methods, in particular in the case of mitral-valve surgery. In the case of mitral-valve surgery, the opening of the ribcage of a patient and the use of a heart-lung machine were previously still necessary.

It is known from the state of the art that such surgeries in the case of heart-valve procedures can also be performed on a beating heart; see the disclosure in WO 2006/078694 A2. Reconstruction and replacement are thus possible by using minimally-invasive surgery, such as with an open thorax method.

A distinction is to be made between an aortic-valve reconstruction and a mitral-valve reconstruction. The mitral-valve reconstruction is a restoration of the valve function with preservation of the mitral valve (bicuspid valve). For successful repair of the valve function of a mitral valve in the interior of a human heart, the various components of the mitral valve are therefore to be studied and their possible defects are to be verified. The study is done, i.a., using diagnostics before surgery, e.g., with a heart catheter and echocardiography.

The mitral valve consists of four functional components, with the two leaflets (mitral-valve leaflets) consisting of an anterior leaflet (cupis anterior) and a posterior leaflet (cupis pasterior), the mount of the leaflets in the mitral-valve ring (mitral-valve annulus), the tendinous cords (Chordae tendineae), with which the leaflets are fastened to move on the papillary muscles, and the papillary muscles themselves, which end in the myocardium. For repair of each individual component, a different surgical instrument and/or an implant is/are available.

The repair of tendinous cords, e.g., by implanting artificial threads as a replacement, is also considered to be mitral-valve reconstruction. From the state of the art—U.S. Pat. No. 8,758,393 B2 and U.S. Pat. No. 9,192,374 B2—a device for minimally-invasive repair of tendinous cords of a (prolapsed) mitral-valve leaflet is known. The disruption of one or more Chordae tendineae that are inserted into the leaflets of the mitral valve is referred to as a tendinous cord rupture. In this case, a torn tendinous cord (severed Chordae), which causes a valve regurgitation, is replaced by an artificial thread (artificial Chordae), whereby the artificial thread is fastened, on the one hand, to the leaflet of the mitral valve of the left atrium and, on the other hand, to the epicardium of the top (the apex) of the left chamber of the heart (left ventricle) in order to prevent the atrioventricular valve (valve leaflets) from slamming back into the atrium (left atrium) during the systole. The access of the instrument for inserting an implant made of artificial tendinous cords (artificial Chordae) is carried out via an incision (lateral LV incision by the true apex) by the myocardium at the top (apex) of the heart in the left ventricle. In order to reach the site of a torn tendinous cord (severed Chordae) in the heart with the minimally-invasive mitral-valve surgery, it is necessary to perform a left lateral ribcage opening (left anterolateral mini-thoracotomy). The instrument is inserted into the left ventricle through the opening into the apex and thus picks up the valve leaflet that was damaged by insufficiency. The instrument guides a two-fold artificial tendinous cord through the valve leaflet and fastens the latter using a loop, by which the valve leaflet is picked up. The two ends of the tendinous cord are tied on the apex outside of the epicardium, after the necessary length of the tendinous cord was determined via various measuring methods, e.g., the echocardiography according to the TEE method. Previously, the opening to the apex of the heart was still sutured. However, this instrument is not suitable for the insertion of a torn tendinous cord (severed Chordae) into the left ventricle of the heart when access is gained via the left atrium.

U.S. Pat. No. 9,044,221 B2 shows another heart-valve-repair system on the beating heart for the use of minimally-invasive surgery. A surgical method with use of an exchangeable repair system is described. The repair system consists of various components, which are assembled to form a device. For the application of the method, access between the ribs in the left area of the thorax is necessary, in order to be able to open the top of the heart wall and to provide an access. The access is able, just like in the case of a trocar, to take up various components of the device. The assembled and locked arrangement of the device is then advanced as a unit through the access into the left chamber of the heart. The monitoring of the advance of the device is done by imaging methods. With the device, after the tissue is gripped, an artificial thread, using a sewing cartridge, on the one hand, can be fastened to a heart-valve leaflet with a knot (girth hitch knot) and on the other hand, can be sutured to a papillary muscle in order to reduce a valve regurgitation. Also, the use of a knot pusher and the tying of threads on the epicardium on the outside of the heart in the area of the apex are possible. Also, this instrument and implant are not suitable for the insertion of a torn tendinous cord (severed Chordae) into the left ventricle of the heart when the access via the right area of the thorax into the left atrium is carried out.

The repair and/or correction of the dysfunctional heart valves can also be carried out by the insertion of a heart valve implant, as disclosed in U.S. Pat. No. 8,480,730 B2, U.S. Pat. No. 8,888,844 B2, U.S. Pat. No. 8,894,705 B2 and U.S. Pat. No. 9,232,999 B2. Here, this is not a question of the application of inventive surgical instruments or devices with whose help mitral-valve insufficiencies can be eliminated, but rather a mitral spacer. The mitral spacer is a valve implant that can be inserted into an opening and closing opening of a mitral valve, in order to prevent a reflux of blood from the ventricle into the left atrium in the case of a contraction of the left ventricle. The valve implant consists of a shaft that extends along a longitudinal axis of the heart implant and that has a spacer on the upper end, which spacer is made from a large number of segments. The segments can have a different size and shape. The outside surfaces of the segments have the function of being in contact with the valve leaflets when closing the mitral valve. The shaft has an anchor section on the lower end. The anchor section consists of an extension screw (helical tissue anchor), which is engaged by rotating around its axis in the muscular tissue of the heart. How and with which means an extension screw is fastened in the muscle tissue is not disclosed. The insertion of such a valve implant is carried out via the access to the median lengthwise sternotomy, which makes it possible to bring the heart into the corresponding position or via the access of the right thoracotomy. Both methods make possible the access to the left atrium of the heart, looking toward the mitral valve. A catheter that is known to surgeons is used in order to insert the valve implant into the left atrium and to fasten it there and to place the valve body between the two mitral-valve leaflets. The valve leaflet is not fastened to the valve body or the spacer.

A feeding catheter that is inserted percutaneously into the heart and by which the mitral-valve implant is advanced is known from U.S. Pat. No. 8,216,302 B2. The fastening of the mitral-valve implant in the left ventricle is carried out by an anchoring mechanism, which contains an extension screw. The extension screw is inserted into the native heart tissue, the muscle wall of the left ventricle near the top of the heart. The insertion of the extension screw is done by rotating the implant, by which the extension screw penetrates into the muscle tissue. The insertion of the extension screw can also be carried out according to the description. A locking mechanism, consisting of two locking pins that are located in a coupled position in a sleeve, can be rotated and moved using a guide wire, which is guided by the centering sets in the sleeve. The locking mechanism acts on an anchoring wire and a stopping mechanism in order to control the extension screw that is to be inserted into the tissue. In order to avoid the complicated mechanism, it is necessary to develop a new screwing system.

The insertion of an extension screw into a tissue using a device is also known from US 2007/0150000 A1. With the device, two separated tissue flaps in a heart are connected to one another with an extension screw. To this end, a movable device (screw catheter) is pulled up onto the separated tissue flaps by a feeding catheter that can be inserted transvenously into the heart and is brought together by the extension screw that can be screwed in. The now adjoining tissue flaps are bonded to one another by applying a high-frequency voltage.

In surgery of the heart and thorax, in most cases an open operation is performed, in which by opening the thorax, access to the heart is provided. Access is gained in general by means of a median sternotomy, whereby for opening the ribcage, an approximately 25-cm longitudinal incision is made through the sternum. In the case of a thoracotomy, the surgical opening of the thorax is done by an intercostal incision, i.e., by a small incision in the intercostal space. The opening that is created by the sternotomy or thoracotomy is kept clear by a rib spreader, which is used to expand and keep open the ribcage. The opening serves the surgeon as access for surgical procedures. The procedures on the organic body parts are then carried out using a large number of different surgical instruments through the opening that is created in the ribcage. If, for example, the patient's heart is opened outward, various catheters, cannulas and clamps are applied directly to the heart and the major blood vessels. Typically, the aorta is occluded with a vessel clamp around the rising aorta in order to isolate the coronary arteries from the remainder of the arterial system, whereby here occluding is defined as the engaging, the pressing-together, the clamping and holding of a vessel. The surgical instruments that are necessarily used make the bodily opening smaller and thus make it difficult for the surgeon to see what he is doing. In addition, because of the size of the opening and the resulting tissue damage and surgical trauma, a faster healing process in the patient is not to be expected. The drawbacks of a median sternotomy are to be avoided.

In order to meet the requirements imposed by minimally-invasive surgery on heart-valve implants and related surgical instruments, it is necessary to develop new embodiments of heart-valve implants and surgical instruments.

There is a need for a medical heart-valve implant with surgical instruments for use in minimally-invasive surgery, which avoids the above-mentioned drawbacks and deficiencies of the known arrangements, in particular a surgical heart-valve implant, which, on the one hand, is simple and economical in production and, on the other hand, makes it possible to produce a heart-valve implant that is outfitted with a functional geometry that is simple in the economic and handling respects, for the more stringent requirements. This surgical heart-valve implant is to reconstruct again not only organic body parts but rather it is also to give the surgeon the option, based on different conditions in the patient's heart, e.g., to be able to shrink different linear distances between the myocardium and a mitral-valve leaflet and to be able to set a reduced reflux in the valve of the mitral valve. The variably-adjustable reflux is to correspond to various medical inputs.

There is therefore the need to make possible surgery using the minimally-invasive technique (mini-thoracotomy) on the beating heart. Of course, the attending heart surgeon has tested the patient in advance to determine whether a heart-valve repair can be performed with a minimally-invasive method. Anatomical or technical requirements, but also the complexity of the necessary procedure, considerably limit the use of the minimally-invasive method.

From the state of the art, heart-valve implants for minimally-invasive repair of a valve flap in the beating heart of a patient, as previously indicated, are known. A heart-valve implant, in particular for the mitral-valve reconstruction, consists of, for example, a connecting element, such as threads, shafts or wires, which in general extends linearly along a longitudinal axis of the heart-valve implant, whereby the connecting element with a first end and a second end, which are arranged opposite to one another, has an anchor, preferably designed as an extension screw, which has a proximal end and a distal end, whereby the proximal end is arranged on the first end of the connecting element. A fastening means is located on the second end of the connecting element. Such a heart-valve implant is inserted from the left area of the thorax into the left ventricle.

SUMMARY

The object of the invention is to indicate a heart-valve implant, which can be inserted within the framework of the application of minimally-invasive surgery via the right area of the thorax and the left atrium of the heart into the left ventricle using a known catheter and can be anchored there.

An implant is therefore to take on only the size that can be guided by a trocar and/or catheter to the surgical site. In one configuration, the implant is to be equipped with a fastening means. The fastening means is to be able to pick up a mitral valve or a mitral-valve leaflet. The mitral valve or a mitral-valve leaflet must still remain movable with the fastening means, but can be adjustable and limited in its range of motion. A connection of the fastening means with the myocardial tissue of the heart can be provided.

For a solution, a heart-valve implant as well as a heart-valve-implant system are provided according to claims 1 and 10. Configurations are the subject matter of the subclaims.

A hybrid OR scenario in the case of an anesthetized patient can be applied for mitral-valve repair. Then, in the case of a collapsed right lung, multiple lateral small access openings are made in the right ribcage between the $3^{rd}$ or $4^{th}$ intercostal space. This procedure is carried out with the minimally-invasive technique (also called keyhole surgery) and includes, for example, trocars, self-retaining retractors, optics, an atrium top retractor, among other instruments. Advantageously, accesses, e.g., for an aortic clamp and for a heart-lung machine in the application of the minimally-invasive surgical method for implanting a heart-valve implant, are no longer required, by which a reduction in the invasiveness and thus a reduction in stress on the patients are achieved.

In order to be able to penetrate into the heart with the surgical instruments and implants and to eliminate a heart-valve prolapse, in particular a mitral-valve prolapse, it is necessary, for performing a mitral-valve reconstruction, to open the left atrium with a small cut, an incision, and to insert a trocar. The trocar is used, e.g., to accommodate one or more catheters and as an access guide for them as well as for an implant in the left atrium and then further through the opening, which is produced in the valve of a mitral valve or between the mitral-valve leaflets in order to be able to penetrate into the left ventricle of the mitral valve.

In one configuration, the heart-valve implant has a mitral-valve implant that can also be referred to with the product name "MitraPeg." The "MitraPeg" can be formed with three elements. A first element is a spiral anchoring element, which is designed as an extension screw. The second element is a connecting element, consisting of an artificial thread or wire, which is equipped with a clamping means in the form of a sliding ring. The sliding ring creates the connection between a thread and a fastening means. The third element forms the basis of the mitral-valve implant; it relates to a fastening means in order to be able to curtail the movement of a mitral valve or to position it. After being created, all three elements are connected to one another to form a heart-valve implant.

On the one hand, the fastening means can pick up a valve leaflet of a mitral valve and, on the other hand, can produce a connection to the artificial thread or wire, on whose end the anchoring element is arranged. The fastening means can in turn have three elements. The three elements can comprise a tube element, a connecting element and a gripping element. The tube element can have a cylindrical sleeve with a connecting element that is arranged thereon. The connecting element can be made with a wire-like strap, which is connected in an articulated manner to the cylindrical sleeve. In technology, a joint is a rotatable connection between two parts with one degree of freedom. The connection can be configured in such a way that the strap can pivot by 360 degrees around the sleeve. To this end, the strap can be made approximately U-shaped, whereby the one open transverse end of the strap engages in a rotatable manner in each case with a pin in respectively one opening in the sleeve wall and thus can be arranged to pivot on the outside of the sleeve. The two openings in the sleeve wall run transversely through the sleeve or perpendicular to the longitudinal axis of the sleeve and are, viewed in the longitudinal direction of the sleeve, arranged approximately in the center.

The other transverse end, removed from the sleeve, of the wire-like strap can be free of pins and have a through transverse rod, which is arranged as a connecting rod between the two longitudinal legs and connects the latter. The connecting rod is a carrier of a gripping element.

The gripping element can have a leg spring and two spring arms. The leg spring can be a leaf spring made of high-grade steel, for example spring steel or nitinol, and can have two eyes or a groove for accommodating the connecting rod of the strap.

At the same time at the crown of the leg spring, the connecting rod of the strap has a transverse axis, in which the transverse end of the strap, removed from the sleeve, engages. The connection between the connecting element and the leg spring can be configured in such a way that the leg spring can rotate around the connecting rod of the strap. The leg spring thus forms with the strap an articulated connection, which runs perpendicular to the longitudinal axis of the sleeve. On the one hand, the leg spring can be arranged to pivot in a fixed orbit in a specific angle range around the transverse axis in the sleeve, and, on the other hand, the leg spring can itself rotate around the separate transverse axis. Based on this design, the elements and means that are connected tightly to one another are arranged to move via the articulated connections.

In turn, the leg spring can be a carrier of two sheet-type spring arms, which are connected tightly to the leg spring. The two spring arms can be parallel and separated by the leg spring and can have a mouth part with gripping sections. The object of the spring arms and the leg spring is to be able to open and close the mouth part of the gripping element. The leg spring therefore is of special importance since the latter must exert force on the spring arms in order to be able to permanently clamp and hold a valve leaflet between the spring arms or the gripping arms of the mouth part. The purpose of the slightly oval spring arms is to form elastic gripping arms. The spring arms are open at one end and have a distance that is specified by the size of the leg spring. The other end of the spring arm forms the movable gripping arm with the closed mouth part.

Such a heart-valve implant, suitable for an implementation, was disclosed according to the information above in connection with a mitral-valve implant. The implant can also be used in other applications, for example as an implant associated with another heart valve. The aspects of this disclosure are therefore not limited to a mitral-valve implant, but rather the implant can be designed for the use of various heart-valve reconstructions.

Corresponding to the preceding explanations, such a heart-valve implant can be produced and used in surgical procedures on the beating heart. First, the object to be achieved was to minimize the size of the heart-valve implant in order to make it possible to access the heart from the right side of the thorax. Disassembling and minimizing the size of the heart-valve implant before insertion into a heart are made possible. The heart-valve implant can be designed to be in multiple parts. The elements of the heart-valve implant are inserted into the heart individually and made ready there.

The elements can be an anchoring element, a connecting element with clamping means, and a fastening means. The three elements together can form the heart-valve implant.

The minimization of the heart-valve implant's size means that the individual elements can take on only a maximum size, which elements also fit by means of a surgical instrument that is guided in the trocar. The anchoring element and the connecting element do not represent the problem in their size, but rather the surgical instruments that are required for inserting and fastening the elements. Therefore, for the insertion and fastening of the anchoring element that is arranged on the connecting element, an inner surgical instrument in the form of a tube spacer II can be provided. The inner tube spacer II can be suitable with its dimensions to be guided through a trocar that is inserted into the atrium of the heart and through the surgical instrument, inserted into the trocar, in the form of an outer tube spacer. In addition, the inner tube spacer II has to be able to be moved by a fastening means. The tube spacer is referred to here as an inner tube spacer II. It is designed in such a way that it can guide the anchoring element with the connecting element that is arranged thereon through the left atrium and the left ventricle up to the myocardium into the heart and can be fastened there. To fasten the anchoring element, the inner tube spacer II on the insertion end has a clamping means, with which the anchoring element can be screwed into the myocardium. In a simple way, the inner tube spacer II can be detached from the anchoring element and removed from the outer tube spacer.

For that reason, to connect the connecting element that is arranged on the anchoring element to a mitral valve or a mitral-valve leaflet, a fastening means, as described previously and shown in the figures, was developed. The fastening means can have a size of only a few millimeters, designed in such a way that it, using a surgical instrument in the form of an outer tube spacer, can be guided by a trocar. According to another aspect, the fastening means has a gripping means for picking up and clamping a mitral-valve leaflet. In addition, the fastening means can be connected to the connecting element, by which a defined separated connection between the mitral-valve leaflet and the myocardium can be created. The separated connection is fixed in length, i.e., a mitral-valve leaflet can be moved only in the ventricle, but cannot swing back into the atrium. When the length is shortened, however, the connection is movable, i.e., when the mitral valve in the ventricle swings in the direction of the myocardium, the connecting element retracts. A connection between a mitral-valve leaflet and the myocardium that is fixed in length but movable is produced by the insertion of a clamping means into the fastening means, with which the connecting element is clamped in the fastening means. The clamping means consists of a sliding ring. For the insertion of the sliding ring into the fastening means, another surgical instrument in the form of another tube spacer III is available. Even for the insertion of the fastening means into the heart, a special surgical instrument in the form of an outer tube spacer, as shown previously, is required. The outer tube spacer can be inserted through a trocar. In addition, the outer tube spacer is in a position to be able to accommodate the other inner tube spacers I, II, III. For example, with an inner tube spacer I, which is guided through the outer tube spacer, the gripping element of the fastening means is picked up to open and close a mouth part. In the meantime, the outer tube spacer holds the fastening means.

The object, which is to perform minimally-invasive surgery for inserting a heart-valve implant into the beating heart from the right side of the thorax, is achieved with the above-mentioned embodiments.

In order to create a heart-valve implant, in particular a mitral-valve implant, and to employ surgical procedures on the human or animal body by use of minimally-invasive surgery, it can be provided that surgical instruments that are required for inserting a heart-valve implant are configured in such a way that ergonomically-configured feeding and removal devices, with various tube spacers that facilitate handling, are available to the surgeon.

In order to be able to implant such a heart-valve implant in the heart, a system with devices and heart-valve implants, according to claim 10, is available, with which a mitral-valve reconstruction is made possible.

A heart-valve-implant system for minimally-invasive repair of a valve flap in the beating heart of a patient can have the following: an outer tube spacer with lumen for guiding and holding a fastening means and a first inner tube spacer I with lumen for opening and closing a gripping element. In addition, a second inner tube spacer II with lumen can be provided for guiding and screwing in an anchoring element, as well as a third inner tube spacer III for inserting and positioning a clamping means. A heart-valve implant is made ready with these surgical instruments. The heart-valve implant can have a connecting element such as thread or wire, which in general extends linearly along a longitudinal axis of the heart-valve implant, whereby the connecting element is equipped with a first end and a second end, in general opposite one another. An anchoring element, which can be designed as an extension screw with a proximal end and a distal end, can be provided, whereby the proximal end is arranged at the first end of the connecting element, and a fastening means is arranged at the second end of the connecting element.

In addition, the heart-valve-implant system can have a fastening means, designed as a tube element in the form of a cylindrical sleeve, and a connecting element and a gripping element, whereby the connecting element can have a strap that has a free end, which is arranged to pivot in the tube element. A gripping element can be arranged to pivot on the other end of the pivotable connecting element that faces the longitudinal direction of the longitudinal axis, whereby the gripping element can consist of a leg spring, on which two spring arms, parallel and separated by the leg spring and connected tightly to the latter, are arranged, in order to reduce at least partially a reflux of blood through the valve of the heart valve that is located in a closed position.

The gripping element of the heart-valve-implant system has a mouth part, formed by the spring arms, on the fastening side of the gripping element and on the side of the open leg spring facing away as well as lying on the longitudinal axis of the tube element, whereby the mouth part has at least one spacer that is arranged in the mouth part, which spacer creates a predetermined and precisely-defined gap between the gripper jaws of the mouth part, ensuring that the gripper jaws that are equipped with gears do not come to rest directly on one another but rather clamp the tissue atraumatically.

BRIEF DESCRIPTION OF THE DRAWINGS

Below, additional embodiments are explained in more detail with reference to the figures of a drawing. In this case.

Figure 1:
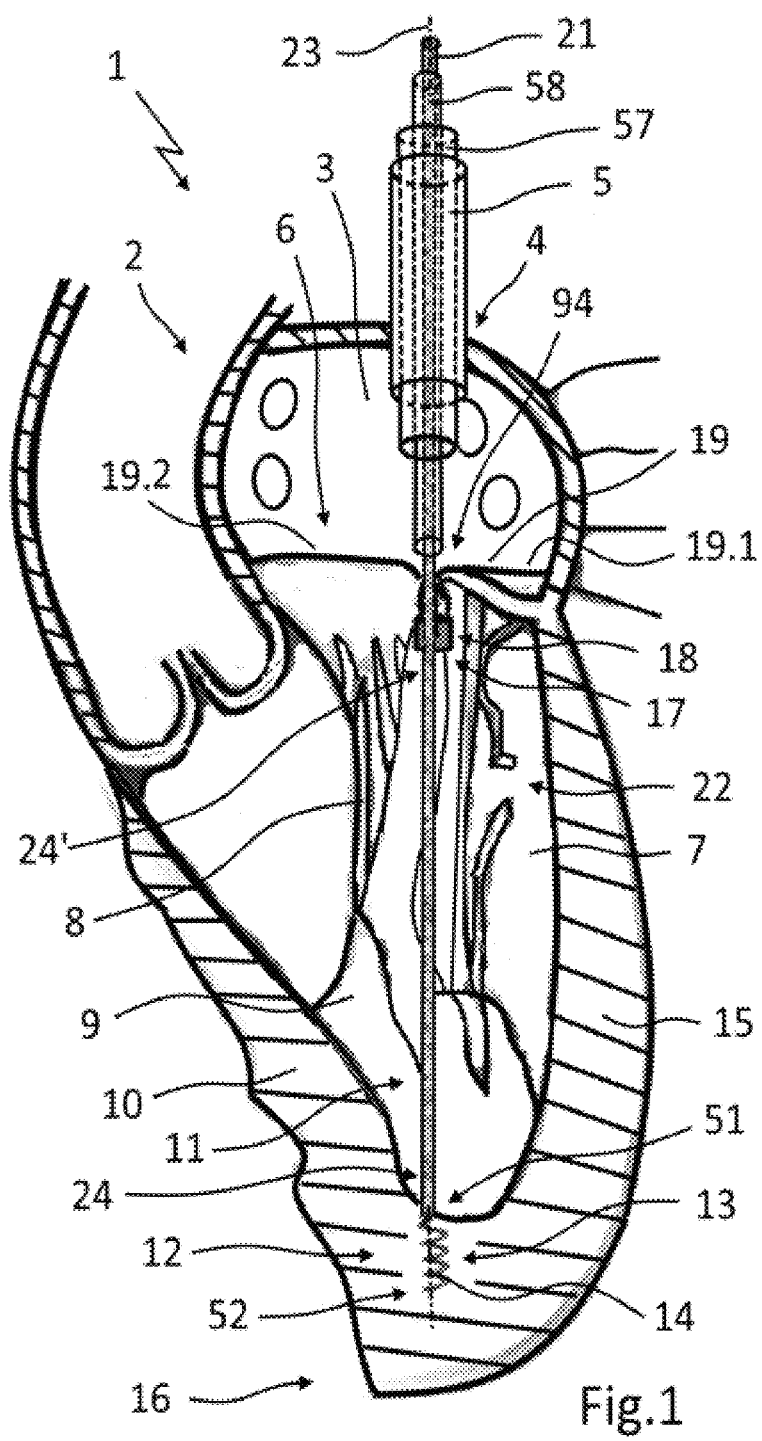
FIG. 1 shows a diagrammatic sectional view of a left chamber of the heart with a left atrium and with an inserted mitral-valve implant in the left ventricle.

The heart 1 that is shown in FIG. 1 in a diagrammatic and basic depiction lies, rotated around its longitudinal axis, in the left space of the thorax, so that the right half of the heart rests more on the anterior chest wall, while the left half of the heart more likely points toward the rear. Starting from the known state of the art, the object of the invention is to develop a heart-valve implant 11, which, when applying minimally-invasive surgery on the beating heart 1 of a patient, can be inserted via the right area of the thorax and the left atrium 3 of the heart 1 and from there into the left ventricle 7 using known surgical instruments and a trocar 5 and can be anchored there.

The left chamber of the heart 2 with the left atrium 3 and an access 4 in the left atrium 3 to the mitral valve 6 as well as to the left ventricle 7 is therefore shown. The access 4 is created via the indicated trocar 5, an outer tube spacer 57, and an inner tube spacer I 58. The outer tube spacer 57 is guided by a trocar 5, and the inner tube spacer I 58 is guided by the outer tube spacer 57. The inner tube spacer I 58 is exchanged in the course of the surgery by another tube spacer II 59; see FIG. 4c. The left ventricle 7 is structured into an inflow and outflow path. It is separated from the atrium 3 by the mitral valve 6. The mitral valve 6 is connected by tendinous cords (Chordae tendineae) 8 to the papillary muscles 9, which originate on the ventricle wall 10 and therefore ensure that the mitral valve 6 during its valve closure and during the exertion phase (systole) of the left chamber 7 does not rebound too violently into the left atrium 3. In the left ventricle 7, the inserted mitral-valve implant 11 can be seen. On the distal end 12, the mitral-valve implant 11 has an anchoring element 13, whereby the anchoring element 13 consists of a corkscrew-like extension screw 14. The insertion of other anchoring means from the known state of the art is conceivable. The screwed-in extension screw 14 is located in the myocardial tissue 15 in the area of the apex, the so-called top heart area 16. In addition, the mitral-valve implant 11 on the proximal end 17 has a fastening means 18, which is fastened to a mitral-valve leaflet 19. A mitral valve 6 consists of two leaflets 19.1, 19.2: the anterior leaflet (Cuspis anterior) 19.1 and the posterior leaflet (Cuspis posterior) 19.2. According to FIG. 1, the mitral-valve implant 11 is attached by way of example to the anterior damaged leaflet 19.1. A connecting element 20 is arranged between the anchoring element 13 and the fastening means 18. The connecting element 20 consists of an artificial thread 21, which extends in general linearly along a longitudinal axis 23 of the heart-valve implant 11, and, e.g., replaces the absence of the function of one or more torn tendinous cords 22, whereby the connecting element 20 with a first end 24 and a second end 24' is arranged in general opposite to one another and connects a fastening means 18 to the anchoring element 13. The fastening means 18 is described in more detail in FIG. 2a and FIG. 2b. Analogous reference numbers from FIG. 1 are adopted in FIGS. 2a and 2b.

Figure 2A:
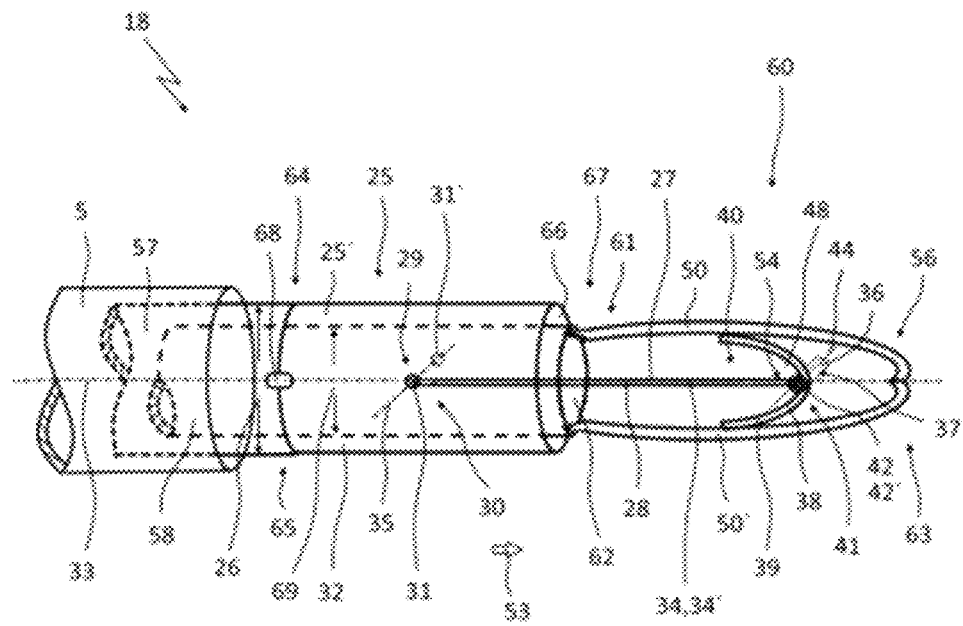
FIG. 2a shows a diagrammatic depiction of the three elements of the fastening means with closed gripping arms in a side view and also in a diagrammatic view.
Figure 2B:
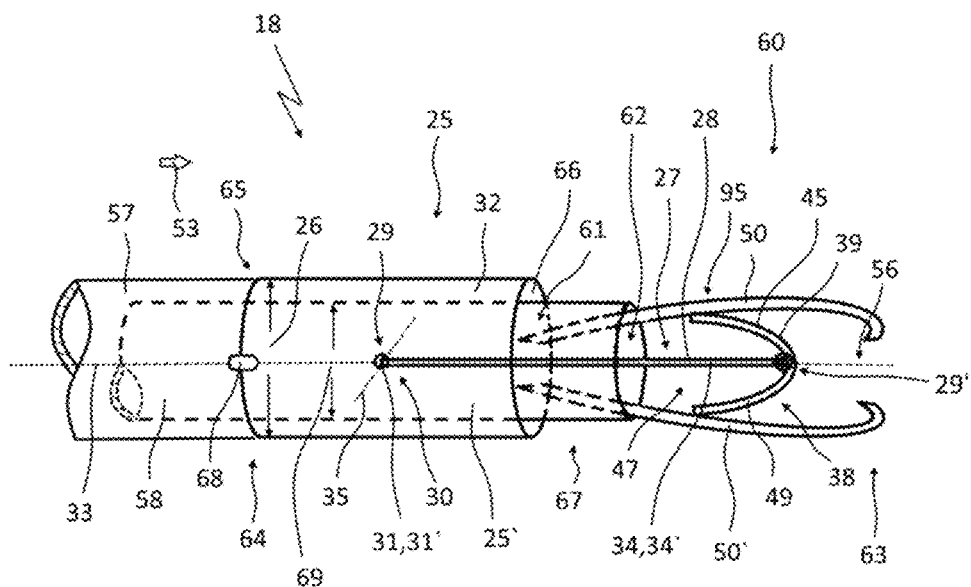
FIG. 2b shows a fastening means with open gripping arms.

In a diagrammatic depiction and side view, FIG. 2a and FIG. 2b show the fastening means 18. According to FIG. 2a, a closed mouth part 56 is provided, and according to FIG. 2b, an open mouth part 56 is provided on the gripping element 60 of the spring arms 50, 50'. The mouth part 56 forms the active side of the heart-valve implant 11 or the fastening side 63 of the heart-valve implant 11 on the mitral valve 6 and is described in more detail in FIG. 2c. The flange side 64 that is opposite to the fastening side 63 on the cylindrical tube element 25 represents the passive side; it is used in the handling or the insertion of the fastening means 18 into the left atrium 3 and subsequently, after the picking up and clamping of a mitral-valve leaflet 19, the insertion into the left ventricle 7.

Before the insertion of the fastening means 18 by a trocar 5 in the atrium 3, the cylindrical tube element 25 of the fastening means 18 is detachably connected to an outer tube spacer 57 with a known type of fastening. The detachable connecting element 68 (not depicted in more detail) between the tube element 25 is located on the flange side 64 of the tube element 25 and the docking side 65 of the outer tube spacer 57. The outer tube spacer 57 is a surgical instrument (not depicted in more detail here), which is operated by the operator outside of the patient's ribcage. The outside diameter of the outer tube spacer 57 is matched as closely as possible to the outside diameter 26 of the cylindrical tube element 25.

In the next step, the one free end 61 of the gripping element 60 of the fastening means 18 is picked up with an inner tube spacer I 58, which is guided by the outer tube spacer 57 and the cylindrical tube element 25. The outside diameter of the inner tube spacer I 58 is matched as closely as possible to the inner diameter 66 of the thin-walled tube element 25. The picking-up of the gripping element 60 is done in such a way that the opening 62 of the inner tube spacer I 58 accommodates the spring arms 50, 50' on the free end 61 of the gripping element 60. Here, it behaves in such a way that the inside diameter 69 of the opening 62 of the inner tube spacer I 58 is somewhat smaller than the outside periphery of the gripping element 60 and thus also the spring arms 50, 50'. The accommodation of the spring arms 50, 50' of the gripping element 60 in the opening 62 of the inner tube spacer I 58 is done by moving the inner tube spacer I 58 over the spring arms 50, 50' of the gripping element 60. The movement is made, according to FIG. 2a, only until the spring arms 50, 50' are guided approximately into the opening 62. To this end, when the inner tube spacer I 58 is moved, the spring arms 50, 50' that are parallel and separated are pressed together somewhat against one another but only far enough that, on the one hand, the spring arms 50, 50' can be accommodated specifically in the opening 62 of the inner tube spacer I 58, and, on the other hand, the mouth part 56 of the gripping element 60 does not yet open. The pressing-together of the spring arms 50, 50' is made possible since the spring arms 50, 50' are arranged on a leg spring 38. The leg spring 38 can be pressed together when pressure is exerted on the spring arms 50, 50'. This exertion of pressure on the spring arms 50, 50' is carried out using the inner tube spacer I 58. After the two spring arms 50, 50' are accommodated in the opening 62 of the inner tube spacer I 58, the cylindrical tube element 25 is approximately flush with the inner tube spacer I 58 on the fastening side 63 of the fastening means 18.

The creation of the fastening means 18 on the two tube spacers 57, 58 can also be carried out in reverse order, in which the spring arms 50, 50' are first picked up with the inner tube spacer I 58. The picking-up of the spring arms 50, 50' is done by the inner tube spacer I 58 being moved through the inside diameter 66 of the cylindrical tube element 25 from the flange side 64 in the longitudinal direction 53 up to the gripping arm side 67. In the next step, the outer tube spacer 57 is fastened to the cylindrical tube element 25 by the latter being moved ahead with its docking side 65, via the inner tube element I 58 up to the flange side 64 of the cylindrical tube element 25, and being connected to the connecting element 68. If the fastening means 18 is picked up by two tube spacers 57, 58, it can be inserted by the trocar 5 into the left atrium 3. In the left atrium 3, the fastening means 18 is then prepared for engaging a mitral-valve leaflet 19 using the two tube spacers 57, 58.

If the fastening means 18 is inserted by two tube spacers 57, 58 into the left atrium 3, the latter can be used in a first application method for opening and closing the mouth part 56, i.e., for picking up and clamping a mitral-valve leaflet 19, as depicted in the sequence below. By moving the outer tube spacer 57 in the trocar 5, e.g., by retracting relative to the inner tube spacer I 58, which remains stationary, the mouth part 56 of the gripping element 60 can be opened. The opening of the mouth part 56 takes place as follows: the outer tube spacer 57, which is docked on the cylindrical tube element 25, pulls the spring arms 50, 50' of the gripping element 60, which are connected via a strap 28 to the tube element 25, further into the opening 62 of the inner tube spacer I 58. As the spring arms 50, 50' are pulled further into the opening 62 of the inner tube spacer I 58, the latter are further pressed together in the area of the free end 61, and the pressure on the leg spring 38 is increased, by which the mouth part 56 of the gripping element 60 is opened; see FIG. 2b. The principle is similar to a see-saw or a two-sided lever that is mounted in the center and on either side of the pivot point has two lifting arms of approximately the same length. If one lever arm is provided with a weight force at one end or a force acts thereon, the loaded arm drops and the opposite or the other unloaded lever arm moves in the opposite direction.

This principle can be carried over to the gripping element 60 with its spring arms 50, 50'. Each spring arm 50, 50' corresponds to a two-sided lever arm; therefore, only one spring arm 50 needs to be considered as representative in evaluating functionality. Such a spring arm 50 has two free ends. One end 61 is located on the open gripping element 60, and the other end is located on the mouth part 56. A spring arm 50 is fastened approximately in the center on a leg spring 38, so that on either side of the fastening, approximately one lever arm of the same length is made. If a force on one free end 61 of a spring arm 50 (lever arm) is now exerted by the inner tube spacer I 58, on the one hand, the spring arm 50 (lever arm) rotates around the fastening point (pivot point) on the leg spring 38, by which the two free ends 61 of the spring arms 50, 50' are to move on one another and thus approach one another, and, on the other hand, the leg spring 38 is somewhat pressed together. The other end of the spring arms 50, 50', on which the mouth part 56 is arranged, moves opposite, i.e., away from one another, and the mouth part 56 is opened.

The mouth part 56 of the gripping element 60 can, however, also be opened and closed by a second application method of the two tube spacers 57, 58 in order to pick up and clamp a mitral-valve leaflet 19. Of the two tube spacers 57, 58 that are located in the atrium 3, the outer tube spacer 57 is now held in a stationary manner and thus also the cylindrical tube element 25 that is docked thereon. By moving the inner tube spacer I 58 in the longitudinal direction 53 and along the longitudinal axis 33 of the fastening means 18, the inner tube spacer I 58 that is located in the interior of the outer tube spacer 57 and in the interior of the cylindrical tube element 25 can further extend via the spring arms 50, 50' that are located in the opening 62. By the advancing of the inner tube spacer I 58 relative to the outer tube spacer 57, which remains stationary with the cylindrical tube element 25, the mouth part 56 of the gripping element 60 can be opened. The opening of the mouth part 56 is done in such a way that the inner tube spacer I 58 is pushed via the spring arms 50, 50' of the gripping element 60, which are connected via a strap 28 to the tube element 25. The spring arms 50, 50' cannot get out of the way since the latter are connected via the leg spring 38 to the strap 28 and the latter in turn to the tube element 25. With further advancing of the inner tube spacer I 58 via the spring arms 50, 50', the latter slide further into the opening 62 of the inner tube spacer I 58. In this case, the two spring arms 50, 50' that are parallel and separated are further pressed together, by which the mouth part 56 of the gripping element 60 opens; see FIG. 2b.

The mitral-valve implant 11 can be equipped with a fastening means 18. The fastening means 18 is to be able to pick up a mitral-valve leaflet 19, cf. FIG. 1, whereby the mitral valve 6 also has to remain movable, but limited in direction in its range of motion. Limited in direction is defined as the slamming-back of the mitral-valve leaflet 19 in the atrium 3.

The heart-valve implant 11 comprises, for example, three elements. A first element is the anchoring element 13, which is designed as an extension screw 14 and undertakes a fastening of the heart-valve implant 11 in the myocardial tissue 15; see FIG. 1. The second element is a connecting element 20, consisting of an artificial thread 21 or wire, which creates the connection between the anchoring element 13 and the fastening means 18 with support of a clamping means 74. These two elements were already shown in FIG. 1. Another element forms the fastening means 18, which is depicted in more detail here in FIG. 2*a* and in FIG. 2*b*.

The fastening means 18 itself can in turn be made with three elements, for example a tube element 25, a connecting element 27 and a gripping element 60. The tube element 25 is preferably designed as a cylindrical sleeve 25', whereby the sleeve 25' can have in cross-section geometric shapes, such as a square tube, etc., and thus is not bound to the circular shape. On the outside diameter 26 of the sleeve 25', two opposite openings 31, 31' are arranged in the sleeve wall 32. The openings 31, 31' are located on a transverse axis 35, which is perpendicular to the longitudinal axis 33 of the sleeve 25', whereby the openings 31, 31' are arranged approximately in the center, viewed in the longitudinal direction 53 of the sleeve 25'. A connecting element 27 is arranged at the openings 31, 31' and the outer side of the sleeve 25'. The connecting element 27 is made from a wire-like, approximately U-shaped strap 28, which is in articulated connection 29 with the cylindrical sleeve 25'. To this end, the free end 30 of the U-shaped strap 28 has two pins (95, 95'), which are bent inward by at least 90 degrees and whereby in each case a pin engages in a rotatable manner in an opening 31, 31' in the sleeve wall 32. The pins can also be bent inward up to 180 degrees, so that a pin runs parallel to the longitudinal leg 34, in order thus to form a type of eye (96, 96') for accommodating the sleeve wall 32. A non-detachable but articulated connection 29 is thus produced between the sleeve 25' and the connecting element 27. The longitudinal legs 34 of the strap 28 have a length that is significantly longer than half the sleeve length, for example three times half the sleeve length. The length of the strap 28 therefore allows the strap 28 to be able to perform a 360-degree rotation around the sleeve 25', since the transverse leg 36 of the strap 28, which connects the two longitudinal legs 34, 34' to one another, is relatively far away from the sleeve 25'. The transverse leg 36 forms a through connecting rod 37 between the longitudinal legs 34, 34', which is a carrier of a gripping element 60. The gripping element 60 can be made with a leg spring 38, which in turn is a carrier of two spring arms 50, 50'.

Figure 3A:
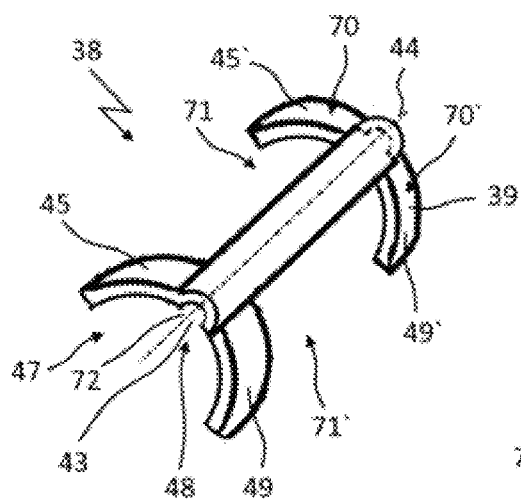
FIG. 3a shows, in a perspective view, an embodiment of a leg spring without spring arms according to FIGS. 2a, 2b.
Figure 3C:
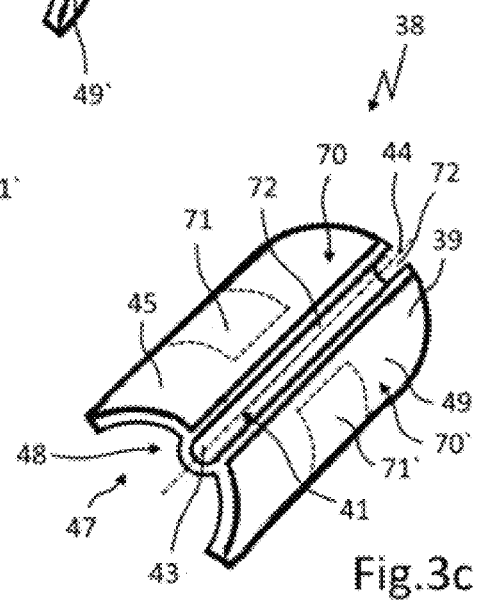
FIG. 3c shows, in a perspective view, another embodiment of a leg spring without spring arms according to FIGS. 2a, 2b.
Figure 3B:
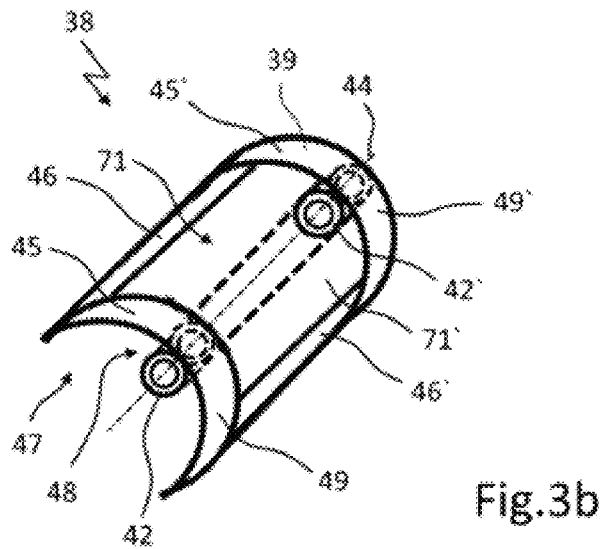
FIG. 3b shows, in a perspective view, an alternative embodiment of a leg spring without spring arms according to FIGS. 2a, 2b.

The leg spring 38 that is designed approximately U-shaped is made from a leaf spring 39, which in the center of the leg area 40 or approximately in the crown 48 of the leg spring 38 has a corresponding connecting element 41 for accommodating a connecting rod 37 of the strap 28. In FIGS. 3*a*, 3*b* and 3*c*, various embodiments of a leg spring 38 are shown. The connecting element 41 can consist of two separated annular eyes 42, 42' (see FIG. 3*b*), which are fixed components of the leg spring 38. The annular eyes 42, 42' are located laterally on the edge of the leg spring 38 and extend inward; see in this regard FIG. 3*b*. As an alternative, the connecting element 41 can also consist of a cylindrical channel 43 or a longitudinal groove 43 (see FIG. 3*a*). The channel 43 or the longitudinal groove 43 runs from one side to the other side of the leg spring 38 or crosswise to the extending leaf spring legs 45, 49; see in this regard the embodiments in FIG. 3*a*. The axis 44 of the annular eyes 42, 42' of the leg spring 38, according to the embodiment of FIG. 3*b*, or the axis 44 of the cylindrical channel 43 or the longitudinal groove 43 of the leg spring 38, according to the embodiment of FIG. 3*a*, runs separate from and parallel to the transverse axis 35 of the openings 31, 31' in the sleeve 25' and also perpendicular to the longitudinal axis 33 of the sleeve 25'. That is to say, the two transverse axes 35 and 44 are parallel and separated, whereby the transverse axis 44 on an orbit 55 (see FIG. 4*b*) can pivot around the transverse axis 35. The connection between the connecting rod 37 of the strap 28 and the corresponding connecting element 41 of the leg spring 38 is configured in such a way that the leg spring 38 can pivot in a rotatable manner around the connecting rod 37. Starting from the crown 48, the U-shaped leg spring 38 points with its open leaf spring legs 45, 49 in the direction of the cylindrical sleeve 25' and the longitudinal legs 34, 34' of the strap 28. The leaf spring legs 45, 45' are thus approximately parallel to the longitudinal axis 33 of the sleeve 25' and are articulated to pivot on the strap 28 and have an opening 47. That is to say, the leg spring 38 that is arranged on the strap 28 performs with the strap 28, on the one hand, a rotation around the transverse axis 35, which runs through the sleeve 25' and, on the other hand, a rotation around the transverse axis 44, which runs through the leg spring 38. The rotation of the leg spring 38 around the two transverse axes 35, 44 can take place at the same time, similar to the principle of a gondola in a Ferris wheel.

The leg spring 38 is in turn a carrier of two spring arms 50, 50'. The two spring arms 50, 50' are tightly connected to the leg spring 38. The connection can be created by technical known methods, such as lasing, welding, riveting, screwing, etc. In this case, a spring arm 50 rests on a leaf spring leg 45, and the other spring arm 50' rests on an opposite leaf spring leg 49 if the leg spring 38 is made only from two leaf spring legs 45, 49. The possibility also exists, however, as shown in FIG. 3*a* and FIG. 3*b*, that the leg spring 38 is made from four leaf spring legs 45, 45', 49, 49'. This means that the one spring arm 50 rests on the two leaf spring legs 45, 45' and the other spring arm 50' rests on the two leaf spring legs 49, 49' that are opposite to the leaf spring legs 45, 45' and is fastened there. The two spring arms 50, 50' are fastened to the leaf spring legs 45, 49 or 45, 45' and 49, 49' of the leg spring 38 in such a way that the latter are separated and approximately parallel in the case of the closed mouth part 56 on the fastening side 63 and with its opposite opening on the free end 61 of the gripping means side 67 and extend parallel to the longitudinal axis 33 of the sleeve 25' and thus to the longitudinal axis 33 of the fastening means 18. The two spring arms 50, 50' that are separate from and parallel to one another have an approximately oval or convex shape, similar to a convex lens. That is to say, the two spring arms 50, 50' are in each case curved outward.

Figure 2C:
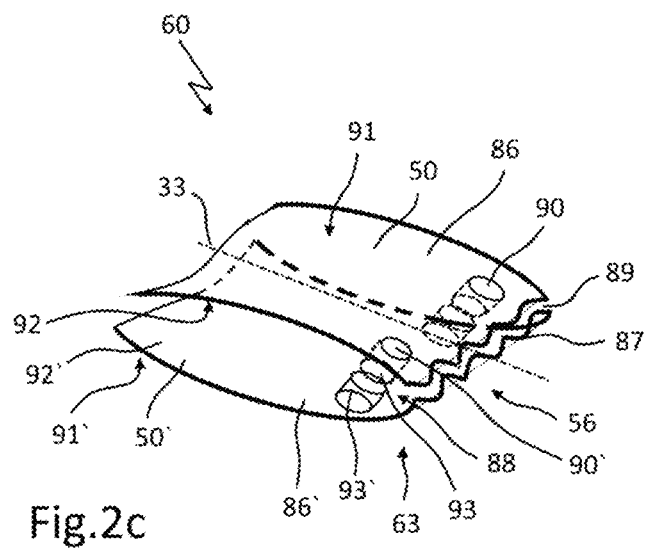
FIG. 2c shows, in a diagrammatic depiction, the mouth part of a gripping element.

In a diagrammatic depiction, FIG. 2*c* shows the mouth part 56 of a gripping element 60 of the fastening means 18. The mouth part 56 is made from the spring arms 50, 50', which are components of the gripping elements 60. The mouth part 56 is arranged on the fastening side 63 of the gripping element 60 and resting on the side of the open leg spring 38 that faces away as well as on the longitudinal axis 33 of the tube element 25, whereby the mouth part 56 has at least one spacer 88 that is arranged in the mouth part 56, which spacer creates a predetermined gap 89 between the gripper jaws 86, 86' of the mouth part 56, by which the gears 87 of the gripper jaws 86, 86' do not come to rest directly on one another. A spacer 88 can be created by, e.g., the imprinting of a bead 90, 90', preferably by two beads per spring arm 50, 50'. The imprinting of beads 90, 90' is done on the outside 91, 91' of the spring arms 50, 50', by which an elevation 93, 93' is produced on the inside 92, 92' of the spring arms 50, 50'. The beads 90, 90' are imprinted opposite to one another in the spring arms 50, 50', so that the elevations 93, 93' created on the inside 92, 92' come to rest on one another when the mouth part 56 is closed and correspond to one another and thus form a spacer 88. An elevation 93, 93' on the inside 92, 92' between the spring arms 50, 50' for forming a spacer 88 can also be carried out by the use of other means.

FIGS. 3a, 3b and 3c show in a perspective view in each case an embodiment of a leg spring 38, which is a component of the gripping element 60. According to FIGS. 2a and 2b, the embodiment of the gripping element 60 consists of two identical, elongated spring arms 50, 50' that are made of rust-resistant, alloyed metal that has specific elastic properties and preferably can consist of nitinol. The spring arms 50, 50' are fastened in the center to a leg spring 38 that consists of rust-resistant metal and are thus held together. The leg spring 38 serves simultaneously as a joint. By pressing together the two spring arms 50, 50' and thus the two leaf spring legs 45, 49 of the leg spring 38 at one end 61 of the spring arms 50, 50' using an inner tube spacer I 58, the mouth part 56 is opened at the other end of the fastening side 63; see FIG. 2b. If the spring arms 50, 50' are released again from the tube spacer I 58, the force that is inherent to the leg spring 38 forces the spring arms 50, 50' apart on the one side of the free end 61 and on the other side of the mouth part 56 forces them back together; see FIG. 2a and FIG. 4a. The gripping element 60 thus works according to the clothespin principle.

The one-piece gripping element 60 consists of a leg spring 38 with spring arms 50, 50' securely arranged thereon, as can be seen from FIGS. 2a and 2b. For better depiction and clarity of a one-piece leg spring 38 and its various embodiments, the depiction of the spring arms 50, 50' in FIGS. 3a, 3b, 3c was omitted, although the latter are, of course, objects on a leg spring 38 and thus the gripping element 60. The reference numbers shown identically in FIGS. 2a and 2b with reference to the gripping element 60 and the leg spring 38 are adopted here by analogy.

It is common to all embodiments of leg springs 38 that the basis consists of a leaf spring 39. These leaf springs 39 are created from elastic spring steel and are designed U-shaped and therefore have an opening 47 between their bent legs. The U-shaped leaf springs 39 therefore form in each case two leaf spring legs 45, 49. The surfaces of the leaf spring legs 45, 49 can have recesses 71, 71' in their surfaces 70, 70', whereby the recesses 71, 71' in the surfaces 70, 70' can be open or closed. Because of the recesses 71, 71', multiple leaf spring legs 45, 45', 49, 49' can appear. Another similarity of the leg springs 38 consists in that a leg spring 38 in its crown 48 has a corresponding connecting element 41 for accommodating a connecting rod 37 of a strap 28 (see FIGS. 2a and 2b). For example, the connecting element 41 can consist of two separated annular eyes 42, 42' (see FIG. 3b), which are fixed components of the leg springs 38. The annular eyes 42, 42' are located laterally on the edge of the leg spring 38 and extend inward in the transverse direction of the leg spring 38 and have a transverse axis 44. The annular eyes 42, 42' of the U-shaped leg spring 38 are located on the inside of the opening 47 of the side that faces the leaf spring legs 45, 49. As an alternative, the annular eyes 42, 42' can be arranged in the crown area 48 of the leg spring 38 but on the outside of the leaf spring legs 45, 49, not depicted, i.e., the side facing away from the opening 47. The annular eyes 42, 42' of the leg spring 38 are designed in such a way that with the connecting rods 37 of a strap 28, they produce an articulated connection 29'.

As an alternative, the connecting element 41 of a leg spring 38 can also consist of a cylindrical channel 43 or a longitudinal groove 43 (see FIG. 3a). The channel 43 or the longitudinal groove 43 runs from the one transverse side to the other transverse side of the leg spring 38 or crosswise to the extending leaf spring legs 45, 49. The cylindrical channel or the longitudinal groove 43 is configured in such a way that the cylindrical channel or the longitudinal groove 43 has a slot 72, which is opened in the direction of the leaf spring legs 45, 49 that are allocated to one another. The slot 72 is opened end-to-end in order to be able to accommodate the connecting rods 37 of a strap 28. The cylindrical channel or the longitudinal groove 43 of the leg spring 38 is designed in such a way that the latter with the connecting rod 37 of a strap 28 produce a secure, but articulated connection 29'. The longitudinal groove 43 has a transverse axis 44, which runs identically to the transverse axis 44 of the annular eyes 42, 42'. Also, this connecting element 41 is located with its cylindrical channel or the longitudinal groove 43 on the inside of the opening 47 of the side that faces the leaf spring legs 45, 49. The leaf spring legs 45, 49 form a one-piece leg spring 38 with the cylindrical channel or the longitudinal groove 43.

In another embodiment of a leg spring 38, see FIG. 3c, the connecting element 41 of a cylindrical channel or a longitudinal groove 43 is not located in the opening area 47 of the leaf spring legs 45, 49 or not on the inside between the leaf spring legs 45, 49, but rather on the outside of the leaf spring legs 45, 49, but nevertheless in the area of the crown 48. Of course, the transverse axis 44 of this embodiment of the leg spring 38 is identical to the transverse axes of the leg springs 38 from FIGS. 3a and 3b. Also, this leg spring 38 is made in one piece and has a slot 72 for accommodating the connecting rod 37 of a strap 28. The cylindrical channel or the longitudinal groove 43 of the leg spring 38 is designed in such a way that the latter with the connecting rod 37 of a strap 28 produce a secure, but articulated connection 29'.

Figure 4A:
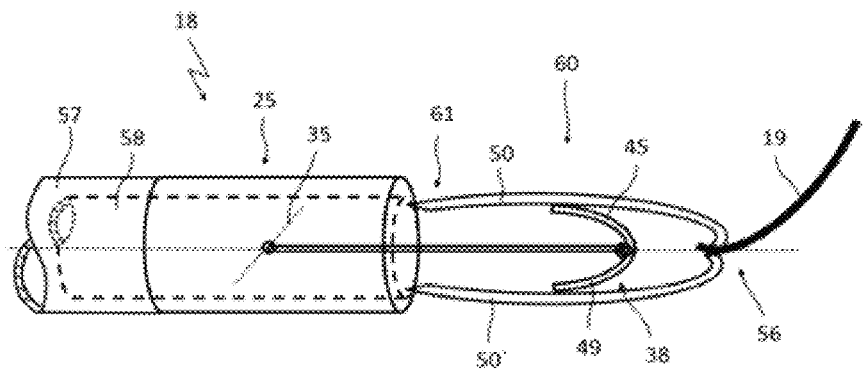
FIG. 4a shows, in a diagrammatic depiction, a fastening means with a clamped-in mitral-valve leaflet.
Figure 4B:
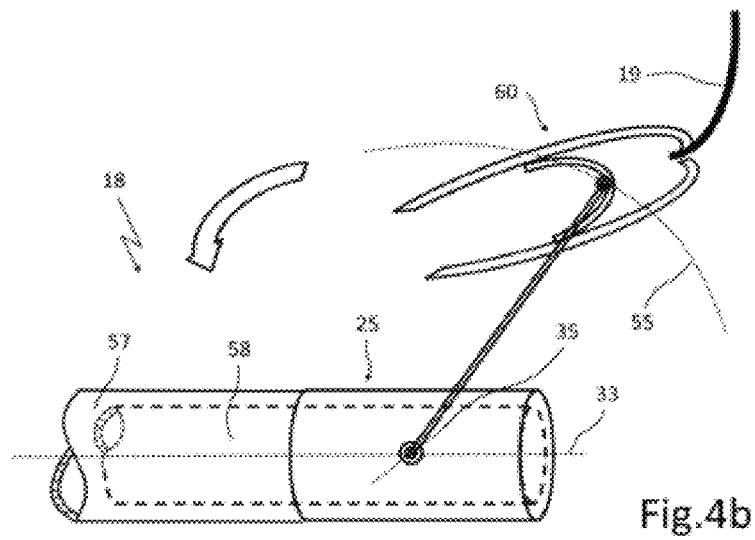
FIG. 4b shows, in a diagrammatic depiction, a fastening means with a clamped-in mitral-valve leaflet during the pivoting process of the gripping element, around the tube element.

In a diagrammatic depiction, FIGS. 4a and 4b show a fastening means 18 with a mitral-valve leaflet 19 that is clamped into the gripping element 60. According to FIG. 4a, the process of picking-up and clamping a mitral-valve leaflet 19 is carried out in the left atrium 3 of the heart 1, whereby the process of opening and closing the mouth part 56 on the gripping element 60 was already described in FIGS. 2a and 2b. FIGS. 3a-3c show the functionality of the gripping element 60. In principle, before a mitral-valve leaflet 19 is gripped, the gripping element 60 is opened and a mitral-valve leaflet 19 is picked up with the open mouth part 56. To pick up a mitral-valve leaflet 19, two tube spacers 57, 58, which transport and operate the fastening means 18, are advanced in the direction of the mitral valve 6. The advancing of the fastening means 18 is observed using imaging methods based on known devices. If the open mouth part 56 of the gripping element 60 is located in the correct position in the mitral-valve leaflet 19, the mouth part 56 is closed. The closing of the mouth part 56 is done by retracting the inner tube spacer I 58 with simultaneous holding of the outer tube spacer 57, by which the cylindrical tube element 25 remains stationary. The inner tube spacer I 58 can now be removed. When the tube spacer I 58 is removed, the leg spring 38 is decompressed, and the two leaf spring legs 45, 49 press the two spring arms 50, 50' a certain distance apart on the free ends 61. On the opposite end of the spring arms 50, 50', on which the mouth part 56 is arranged, the maximum force of the leg spring 38 now acts on the mouth part 56 in such a way that the mitral-valve leaflet 19 that is located in the mouth part 56 is clamped. The clamping is done as described in FIG. 2c.

In the next step, the pivoting of the gripping element 60 around the transverse axis 35 of the cylindrical tube element 25 and the insertion of the fastening means 18 into the left ventricle 7 are carried out in order to position the latter there, on the one hand, and to fasten it in the myocardial tissue 15, on the other hand. This process is shown in FIGS. 4b and 4c.

Figure 5:
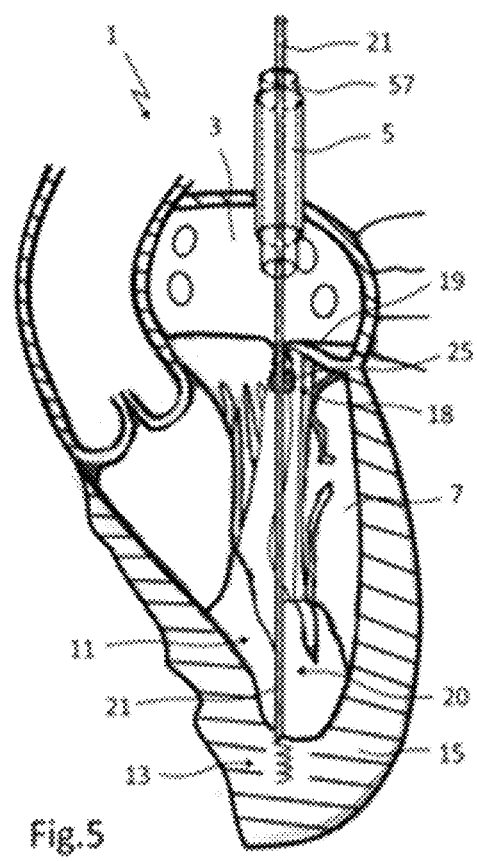
FIG. 5 shows, in a diagrammatic depiction, a heart-valve implant that is anchored in the left ventricle.

FIG. 4b shows, in a diagrammatic depiction, a fastening means 18 with a clamped mitral-valve leaflet 19 with the gripping element 60 in the pivoting process. In order to convey the fastening means 18, which has already picked up and clamped a mitral-valve leaflet 19, from the left atrium 3 (i.e., fastening means 18 is still located above the mitral valve 6) into the left ventricle 7 below the mitral valve 6, it is necessary to perform another handling or advancing of the outer tube spacer 57 with the outer tube spacer 57 (see, i.a., in FIG. 1). To this end, the outer tube spacer 57 first inserts the cylindrical tube element 25 that is fastened to it in a detachable manner and then the gripping element 60 that is arranged on the tube element 25 through the valve opening 94 in the mitral valve 6 into the left ventricle 7. The pivoting process of the gripping element 60 around the tube element 25 is completed when the gripping element 60 comes to rest outside on the outer tube spacer 57. The gripping means 60 that is arranged to pivot on the fastening means 18, with clamped mitral-valve leaflet 19 below the mitral valve 6 in the left ventricle 7, is located in this position, as shown in FIGS. 1 and 5. Also, this handling, the advancing of the fastening means 18 using the outer tube spacer 57 into the left ventricle 7, is monitored using known imaging methods. Monitoring is key in the guiding of the outer tube spacer 57.

Figure 4C:
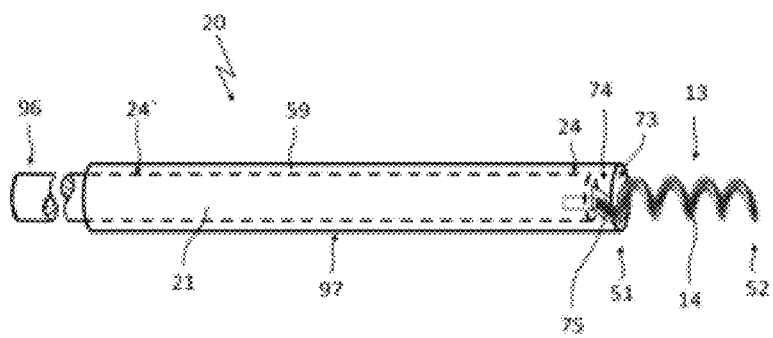
FIG. 4c shows, in a diagrammatic depiction, a surgical instrument for guiding and fastening the anchoring element that is arranged on the connecting element.

The fastening of the fastening means 18 in the myocardial tissue 15 of the left ventricle 7 is shown in a diagrammatic depiction in FIG. 4c, and the positioning of the heart-valve implant 11 is shown in FIG. 5.

FIG. 4c shows, in a diagrammatic depiction, a surgical instrument for guiding and fastening the anchoring element 13, arranged on the connecting element 20, in the myocardial tissue 15. The surgical instrument is referred to here as an inner tube spacer II 59. The inner tube spacer II 59 is equipped in the interior with a connecting element 20 and an anchoring element 13, whereby the connecting element 20 is tightly connected to the anchoring element 13. The connecting element 20 consists of a thread 21, which is produced from polytetrafluoroethylene (PTFE). The one (second) end of the thread 21 of the connecting element 20 is located outside of the thorax of the patient, while the other (first) end 24 of the thread 21 is tightly connected to the proximal end 51 of the anchoring element 13. The anchoring element 13 consists of an extension screw 14, which can be produced from a nickel-titanium alloy, preferably from nitinol. On the insertion end 73, the inner tube spacer II 59 has a clamping means 74 to guide and fasten the helical anchoring element 13. The clamping means 74 can be designed as a helical groove 75 in the tube wall 76, whereby the helical groove 75 forms a curve that is arranged with a constant incline in the wall of the inner tube spacer II 59. The slope and clearance of the helical groove 75 correspond to the slope of the right-hand extension screw 14. The helical groove 75 is designed to be relatively short on the insertion end 73 of the inner tube spacer II 59 and picks up the extension screw 14 on the proximal end 51 when the inner tube spacer II 59 is rotated clockwise.

Even before the inner tube spacer II 59 is inserted by a trocar 5 and through the hole 66 (inside diameter) of the fastening means 18 into the left ventricle 7, the connecting element 20 and the anchoring element 13 have been inserted into the interior of the tube spacer II 59. The anchoring element 13 is located on the insertion end 73 of the tube spacer II 59, whereby the proximal end 51 of the extension screw 14 is located in the helical groove 75. The selection of the size of the extension screw 14 that is to be used was determined before the surgery in order to react to the varying thickness of the myocardial tissue 15 in the area of the apex 16. Thus, various lengths of extension screws 14 are available. The distal end 52 of the extension screw 14 is now inserted into the myocardial tissue 15 by clockwise rotation of the tube spacer II 59. If the end position of the extension screw 14 in the myocardial tissue 15 is reached, the connection to the extension screw 14 is achieved by simple counter-clockwise rotation of the tube spacer II 59. The proximal end 51 of the extension screw 14 slides out from the helical groove 75 in the case of the counter-clockwise rotation of the tube spacer II 59. The inner tube spacer II 59 is now removed by retraction from the fastening means 18 and the trocar 5.

Figure 6:
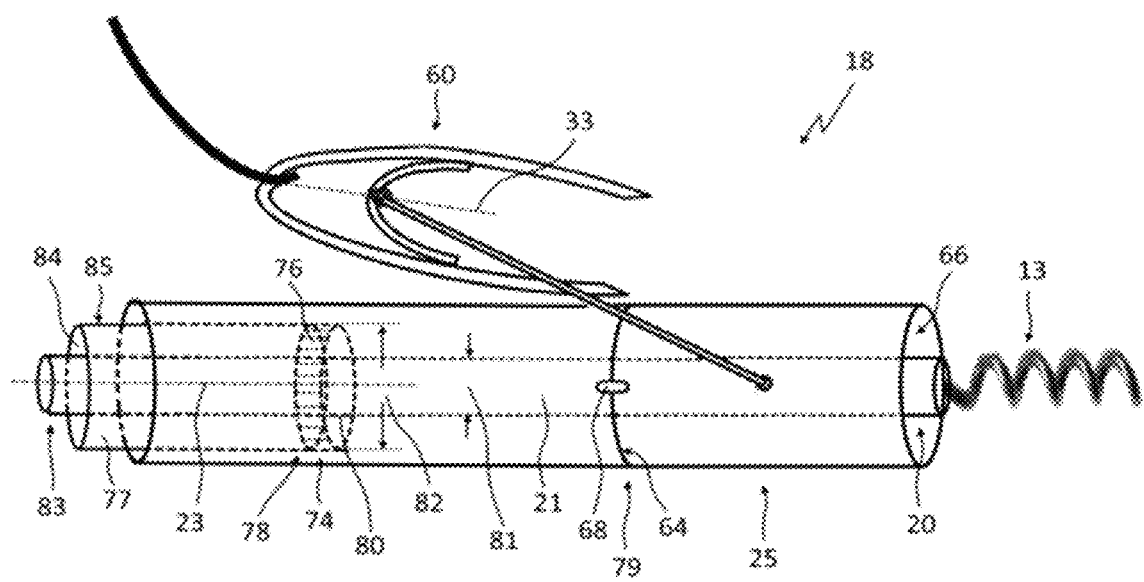
FIG. 6 shows, in a diagrammatic depiction, the creation of a connection between a fastening means and an anchoring element with the support of a clamping means.
Figure 7A:
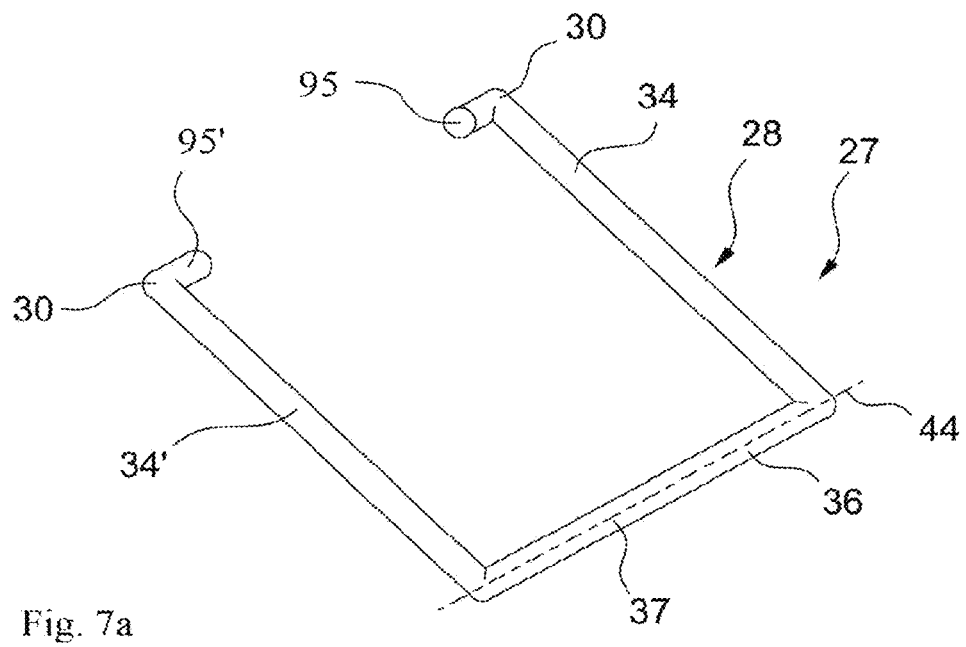
FIG. 7a shows, in a diagrammatic depiction, the free end of the U-shaped strap having two pins.
Figure 7B:
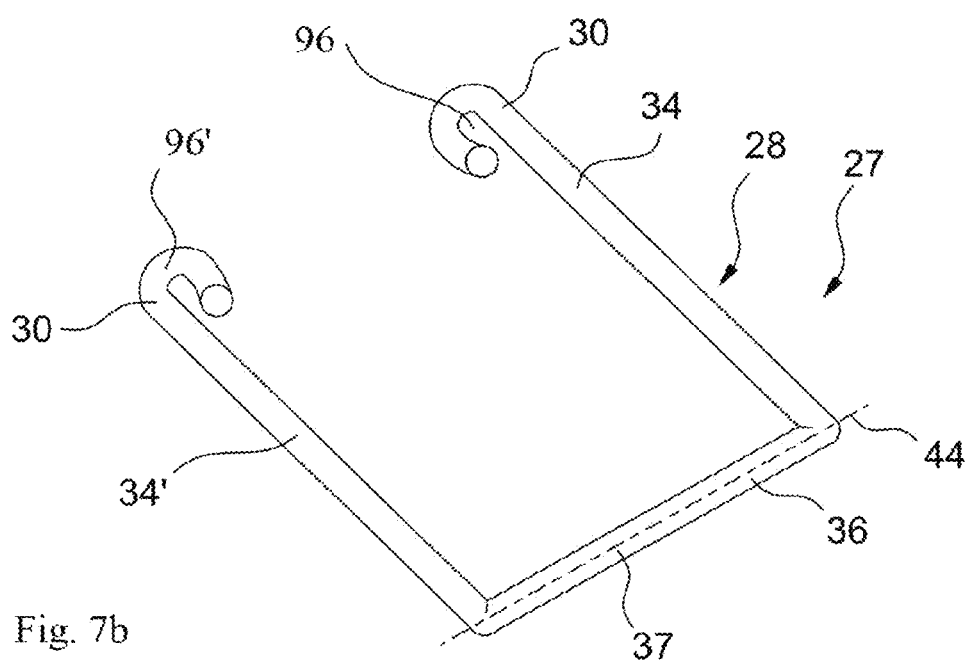
FIG. 7b shows, in a diagrammatic depiction, the free end of the U-shaped strap having two eyes.

As FIG. 5 shows, in a diagrammatic depiction, a heart-valve implant 11 is now located in the left ventricle 7 of the heart 1, whereby the fastening means 18 has picked up a mitral-valve leaflet 19 and the spiral anchoring element 13 is anchored in the myocardial tissue 15. The thread 21 of the connecting element 20 at this time still runs from the anchoring element 13 through the cylindrical tube element 25 of a fastening means 18, through an outer tube spacer 57 that is docked on the fastening means 18 and from there through the trocar 5 that is inserted in the left atrium 3 up to outside of the thorax. The two inner tube spacers I, II 58, 59 were already previously removed. At present, as FIG. 6 shows, only the outer tube spacer 57 is still used on the fastening means 18. For guiding the outer tube spacer 57, in addition the inserted trocar 5 is used. For creating the heart-valve implant 11, it is necessary still to produce a connection between the connecting element 20 and the fastening means 18. The connection is shown in FIG. 6, whereby reference numbers from the above-mentioned figures can be indicated therein.

In a diagrammatic depiction, FIG. 6 shows the creation of the connection between a fastening means 18 and an anchoring element 13 using the connecting element 20 and a clamping means 74. The connecting element 20 consists of a thread 21, which reaches from the anchoring element 13 to outside of the thorax and runs through the inside opening 66 of the fastening means 18. A clamping means 74 is put onto the outward-lying end 83 of the thread 21. To move the clamping means 74 onto the thread 21, an inner tube spacer III 77 is used again. The inner tube spacer III 77 accommodates in its hole 84, on the one hand, a thread 21 and a clamping means 74. On the other hand, the outside diameter 85 of the inner tube spacer III 77 passes into the outer tube spacer 57. With the front side 78 of the tube spacer III 77, the clamping means 74 is moved onto the thread 21 along the longitudinal axis 23 to the fastening site 79. The fastening site 79 is located on the flange side 64, at the input of the inner opening 66 of the cylindrical tube element 25. The material of the clamping means 74 can preferably consist of PTFE; other materials are also conceivable. The hole 80 in the clamping means 74 is approximately matched to the diameter 81 of the thread 21, provided that the thread 21 in the clamping means 74 can be moved with difficulty or the clamping means 74 can be moved only with a certain force on the thread 21. The hole 80 and the diameter 81 form a tight fit. The same applies to the outside diameter 82 of the clamping means 74 and the inside diameter 66 of the cylindrical tube element 25. The outside diameter 82 is slightly larger than the inside diameter 66, by which in turn a tight fit is produced. To insert the clamping means 74 into the fastening means 18, the threads 21 of the connecting element 20 and the hole 84 of the inner tube spacer III 77 are lubricated because of the tight fits. The clamping means 74 can comprise various embodiments. In the case of an embodiment of the clamping means 74, the latter is designed cylindrically as sliding ring 76. In another embodiment, the clamping means 74 is designed like a frustum, similar to a bottle stopper (not depicted). The smaller diameter of the frustum, which is slightly smaller than the inside opening 66 of the cylindrical tube element 25, is first inserted using the tube spacer III 77. The clamping effect takes hold on the lateral surface of the frustum. The positioning of the fastening means 18 is carried out in the left ventricle 7 using, e.g., the sliding ring 76. The sliding ring 76 is inserted in the optimal position of the fastening means 18 in the mitral valve 6 into the cylindrical tube element 25. The determination of the optimal position of the fastening means 18 is further carried out with the known imaging measuring process, whereby the blood reflux during the contraction of the left ventricle in the left atrium 3 is also determined. The optimal position is reached when the blood reflux is at its bare minimum. If the optimal position is not yet reached, the sliding ring 76 is further advanced onto the thread 21 along the longitudinal axis 23 in the direction of the anchoring element 13 with the tube spacer III 77. While the sliding ring 76 is advancing onto the thread 21, on the one hand, the thread 21 is fixed outside of the thorax, and the fastening element 18 is kept stationary with the outer tube spacer 57. After the successful placing of the sliding ring 76 in the fastening means 18, the heart-valve implant 11 is made fully formed and the inner tube spacer III 77 can be retracted and removed. The tube spacer III 77 is now replaced by a known surgical instrument (not depicted). With the surgical instrument, the thread 21 on the sliding ring 76 can be tied and cut off, whereby other types of fastening are also conceivable. After the remaining thread 21 is removed from the heart 1 and the thorax as well as the surgical instrument, the outer tube spacer 57 is also separated from the fastening means 18. To this end, the outer tube spacer 57 is detached from the connecting point 68, e.g., by rotating, depending on how the connecting point 68 is configured. After the outer tube spacer 57 is removed from the valve opening of the mitral valve 6, the gripping element 60 pivots on the longitudinal axis 23 of the heart-valve implant 11. The longitudinal axis 33 of the gripping element 60 and the fastening means 18 is now identical to the longitudinal axis 23 of the connecting element 20 and the anchoring element 13. Both longitudinal axes 23, 33 now form a common axis. The insertion of an inventive heart-valve implant 11 into the left ventricle 7 of a heart 1 is thus completed.

The previous embodiment, according to FIGS. 1 to 6, shows a mitral-valve implant, which, once set up in the left ventricle and inserted to form a mitral-valve leaflet, eliminates regurgitation. Regurgitation is a process in which the contents from the cavity of the heart not only take the usually provided path but rather partially or predominantly flow back in the other direction. This process is pathological in humans and in many kinds of animals. To eliminate regurgitation, additional embodiments in the case of the heart-valve implant, in particular in the case of the fastening means of the heart-valve implant, are possible and therefore not limited to the example embodiment. The latter also relates to the technique for making the connection between the connecting element and the fastening means.

Reference Symbol List

| | | | |
|---|---|---|---|
| 1 | Heart | 30 | Free end (of 28) |
| 2 | Left chamber of the heart | 31, 31' | Openings |
| 3 | Left atrium | 32 | Sleeve wall |
| 4 | Access | 33 | Longitudinal shaft (of 25, 25') |
| 5 | Trocar | 34, 34' | Longitudinal legs (of 28) |
| 6 | Valve/mitral valve | 35 | Transverse shaft |
| 7 | Left ventricle | 36 | Transverse leg |
| 8 | Tendinous cord | 37 | Connecting rod |
| 9 | Papillary muscles | 38 | Leg spring (of 60) |
| 10 | Ventricle wall | 39 | Leaf spring |
| 11 | Mitral-valve implant | 40 | Leg area |
| 12 | Distal end (of 11) | 41 | Connecting element |
| 13 | Anchoring element | 42, 42' | Annular eyes |
| 14 | Extension screw | 43 | Channel/longitudinal groove |
| 15 | Myocardial tissue | 44 | Transverse shaft |
| 16 | Heart area (apex) | 45, 45' | Leaf spring legs |
| 17 | Proximal end (of 11) | 46, 46' | Crossbars |
| 18 | Fastening means | 47 | Opening of the leaf spring leg |
| 19 | Mitral-valve leaflet | 48 | Crown |
| 19.1 | Anterior valve leaflet | 49, 49' | Leaf spring legs |
| 19.2 | Posterior valve leaflet | 50, 50' | Spring arms |
| 20 | Connecting element | 51 | Proximal end (of 14) |
| 21 | Thread | 52 | Distal end (of 14) |
| 22 | Torn tendinous cord | 53 | Longitudinal direction |
| 23 | Longitudinal shaft (of 11) | 54 | End (of 28) |
| 24, 24' | First, second end(s) | 55 | Orbit |
| 25, 25' | Tube element/sleeve | 56 | Mouth part |
| 26 | Outside diameter | 57 | Outer tube spacer |
| 27 | Connecting element (between 25, 38) | 58 | Inner tube spacer I |
| 28 | Strap | 59 | Inner tube spacer II |
| 29, 29' | Articulated connection | 60 | Gripping element |
| 61 | Free end (of 60) | 90, 90' | Beads (in 50, 50') |
| 62 | Opening (in 58) | 91, 91' | Outer sides (of 50, 50') |
| 63 | Fastening side (of 18, 60) | 92, 92' | Inner sides (of 50, 50') |

-continued

| Reference Symbol List | | | |
|---|---|---|---|
| 64 | Flange side (of 18, 25) | 93, 93' | Elevations |
| 65 | Docking side (of 25) | 94 | Valve opening |
| 66 | Inner diameter/opening (of 25) | | |
| 67 | Gripping arm side | | |
| 68 | Connecting point (between 25, 57) | | |
| 69 | Inner diameter (of 58) | | |
| 70, 70' | Surface/outside | | |
| 71 | Recess | | |
| 72 | Slot | | |
| 73 | Insertion end | | |
| 74 | Clamping means | | |
| 75 | Helical groove | | |
| 76 | Sliding ring | | |
| 77 | Tube spacer | | |
| 78 | Front side | | |
| 79 | Fastening-connecting point | | |
| 80 | Hole (of 76) | | |
| 81 | Diameter (of 21) | | |
| 82 | Outside diameter (of 76) | | |
| 83 | Thread end | | |
| 84 | Hole (of 77) | | |
| 85 | Outside diameter (of 77) | | |
| 86, 86' | Gripper jaws (of 56) | | |
| 87 | Gear | | |
| 88 | Spacer | | |
| 89 | Gap (of 56) | | |

The invention claimed is:

1. A heart-valve implant (11) for minimally-invasive repair of a valve flap (6) in a beating heart (1) of a patient, comprising
a first connecting element (20) having a first end (24) and a second end (24') opposite one another,
an anchoring element (13), which has a proximal end (51) and a distal end (52), wherein the proximal end (51) is arranged on the first end (24) of the first connecting element (20) and a fastening means (18) is arranged on the second end (24') of the first connecting element (20),
wherein the fastening means (18) contains the following:
a tube element (25);
a second connecting element (27); and
a gripping element (60), wherein
the second connecting element (27) has a free end (30), which is arranged to pivot in the tube element (25), and
on the other end (54) of the pivotable second connecting element (27) along a longitudinal axis (33) in a longitudinal direction (53), a leg spring (38) is arranged to pivot, on which two spring arms (50, 50') that are parallel and separated by the leg spring (38) are arranged, and the two spring arms (50, 50') are connected to said leg spring (38); and
a clamping means (74), which connects the first connecting element (20) to the fastening element (18).

2. The heart-valve implant (11) according to claim 1, wherein the tube element (25) with the second connecting element (27) form a first articulated connection (29), and the second connecting element (27) with the gripping element (60) form aft a second articulated connection (29').

3. The heart-valve implant (11) according to claim 1, wherein the tube element (25) is a cylindrical sleeve (25') and has two opposite openings (31, 31') in a sleeve wall (32), resting on a transverse axis (35), wherein the transverse axis (35) is perpendicular to the longitudinal axis (33) of the sleeve (25'), and openings (31, 31'), viewed in the longitudinal direction of the sleeve (25'), are arranged in the center in the sleeve wall (32).

4. The heart-valve implant (11) according to claim 1, wherein the second connecting element (27) forms a strap (28), which comprises two longitudinal legs (34, 34') and a transverse leg (36), wherein a pin or an eye is arranged on free ends (30) of the longitudinal legs (34, 34'), and the transverse leg (36) forms a connecting rod (37) with a transverse axis (44), which is separate from and parallel to the transverse axis (35) in the sleeve (25') and a connecting rod (37) is a carrier of a leg spring (38).

5. The heart-valve implant (11) according to claim 1, wherein the leg spring (38) of the gripping element (60) is made U-shaped from a leaf spring (39) and has at least two leaf-spring legs (45, 45', 49, 49'), wherein a further connecting element (41) that corresponds to the connecting rod (37) of the strap (28) and with a transverse axis (55) is arranged in an inside crown (48) of a leg area (40).

6. The heart-valve implant (11) according to claim 5, wherein said further connecting element (41) is made from at least one annular eye (42, 42'), a cylindrical channel (43), a longitudinal groove (43) or a slot (72).

7. The heart-valve implant (11) according to claim 5, wherein said further connecting element (41) is arranged on the outside (70) of the leaf-spring legs (45, 45', 49, 49') in the leg area (40) of the side of an opening (47) of the leaf-spring legs (45, 45', 49, 49') that faces away.

8. The heart-valve implant (11) according to claim 5, wherein the leaf spring (39) of the leg spring (38) in a surface (70) has at least one recess (71) in the leaf-spring leg (45, 49).

9. The heart-valve implant (11) according to claim 1, wherein the gripping element (60) has a mouth part (56) that is formed by the spring arms (50, 50'), which mouth part is arranged resting on a fastening side (63) of the gripping element (60) and on a side of the open leg spring (38) that faces away as well as on the longitudinal axis (33) of the tube element (25), wherein the mouth part (56) has at least one spacer (88) that is arranged in the mouth part (56) and that creates a predetermined gap (89) between gears (87) of gripper jaws (86) in the mouth part (56).

10. A heart-valve-implant system for minimally-invasive repair of a valve flap (6) in a beating heart (1) of a patient, comprising
  an outer tube spacer (57) with lumen for guiding and holding a fastening means (18);
  a first inner tube spacer I (58) with lumen for opening and closing a gripping element (60);
  a second inner tube spacer II (59) with lumen for guiding and screwing-in an anchoring element (13);
  a third inner tube spacer III (77) for inserting and positioning a sliding ring (76); and
  a heart-valve implant (11), comprising
    a first connecting element (20), wherein the first connecting element (20) is equipped with a first end (24) and a second end (24') opposite one another;
    said anchoring element (13), which has a proximal end (51) and a distal end (52), wherein the proximal end (51) is arranged on the first end (24) of the first connecting element (20) and said fastening means (18) is arranged on the second end (24') of the first connecting element (20);
    said fastening means (18) designed as a tube element (25) in the form of a cylindrical sleeve (25'); and
    a second connecting element (27), wherein
      the second connecting element (27) has a strap (28), which has a free end (30) that is arranged to pivot in the tube element (25), and
      said gripping element (60) is arranged to pivot on the other end (54) of the pivotable second connecting element (27) along a longitudinal axis (33) in a longitudinal direction (53), and
      said gripping element (60) has a leg spring (38), on which two spring arms (50, 50') that are parallel and separated by the leg spring (38) are arranged, and the two spring arms (50, 50') are connected to said leg spring (38).

11. The heart-valve-implant system according to claim 10, wherein the gripping element (60) has a mouth part (56) that is formed by the spring arms (50, 50'), which mouth part is arranged resting on a fastening side (63) of the gripping element (60) and on a side of the open leg spring (38) that faces away as well as on the longitudinal axis (33) of the tube element (25), wherein the mouth part (56) has at least one spacer (88) that is arranged in the mouth part (56), which spacer creates a predetermined gap (89) between gears (87) of gripper jaws (86) in the mouth part (56).

12. A heart-valve implant (11) for minimally-invasive repair of a valve flap (6) in a beating heart (1) of a patient, comprising
  a first connector (20) having a first end (24) and a second end (24') opposite one another,
  an anchor (13), which has a proximal end (51) and a distal end (52), wherein the proximal end (51) is arranged on the first end (24) of the first connector (20) and a fastener (18) is arranged on the second end (24') of the first connector (20), wherein the fastener (18) contains the following:
  a tube (25);
  a second connector (27); and
  a gripper (60), wherein
    the second connector (27) has a free end (30), which is arranged to pivot in the tube (25), and
    on the other end (54) of the pivotable second connector (27) along a longitudinal axis (33) in a longitudinal direction (53), a leg spring (38) is arranged to pivot, on which two spring arms (50, 50') that are parallel and separated by the leg spring (38) are arranged, and the two spring arms (50, 50') are connected to said leg spring (38); and
  a clamp (74), which connects the first connector (20) to the fastener (18).

13. The heart-valve implant (11) according to claim 12, wherein the tube (25) with the second connector (27) form a first articulated connection (29), and the second connector (27) with the gripper (60) form a second articulated connection (29').

14. The heart-valve implant (11) according to claim 12, wherein the tube (25) is a cylindrical sleeve (25') and has two opposite openings (31, 31') in a sleeve wall (32), resting on a transverse axis (35), wherein the transverse axis (35) is perpendicular to the longitudinal axis (33) of the sleeve (25'), and openings (31, 31'), viewed in the longitudinal direction of the sleeve (25'), are arranged in the center in the sleeve wall (32).

15. The heart-valve implant (11) according to claim 12, wherein the second connector (27) forms a strap (28), which comprises two longitudinal legs (34, 34') and a transverse leg (36), wherein a pin or an eye is arranged on free ends (30) of the longitudinal legs (34, 34'), and the transverse leg (36) forms a connecting rod (37) with a transverse axis (44), which is separate from and parallel to the transverse axis (35) in the sleeve (25') and a connecting rod (37) is a carrier of a leg spring (38).

16. The heart-valve implant (11) according to claim 12, wherein the leg spring (38) of the gripper (60) is made U-shaped from a leaf spring (39) and has at least two leaf-spring legs (45, 45', 49, 49'), wherein a further connecting element (41) that corresponds to the connecting rod (37) of the strap (28) and with a transverse axis (55) is arranged in an inside crown (48) of a leg area (40).

17. The heart-valve implant (11) according to claim 16, wherein said further connecting element (41) is made from at least one annular eye (42, 42'), a cylindrical channel (43), a longitudinal groove (43) or a slot (72).

18. The heart-valve implant (11) according to claim 16, wherein said further connecting element (41) is arranged on the outside (70) of the leaf-spring legs (45, 45', 49, 49') in the leg area (40) of the side of an opening (47) of the leaf-spring legs (45, 45', 49, 49') that faces away.

19. The heart-valve implant (11) according to claim 16, wherein the leaf spring (39) of the leg spring (38) in a surface (70) has at least one recess (71) in the leaf-spring leg (45, 49).

20. The heart-valve implant (11) according to claim 12, wherein the gripper (60) has a mouth part (56) that is formed by the spring arms (50, 50'), which mouth part is arranged resting on a fastening side (63) of the gripper (60) and on a side of the open leg spring (38) that faces away as well as on the longitudinal axis (33) of tube (25), wherein the mouth part (56) has at least one spacer (88) that is arranged in the mouth part (56) and that creates a predetermined gap (89) between gears (87) of gripper jaws (86) in the mouth part (56).

21. A heart-valve-implant system for minimally-invasive repair of a valve flap (6) in a beating heart (1) of a patient, comprising
  an outer tube spacer (57) with lumen for guiding and holding a fastener (18);
  a first inner tube spacer I (58) with lumen for opening and closing a gripper (60);
  a second inner tube spacer II (59) with lumen for guiding and screwing-in an anchor (13);

a third inner tube spacer III (77) for inserting and positioning a sliding ring (76); and a heart-valve implant (11), comprising a first connector (20), wherein the first connector (20) is equipped with a first end (24) and a second end (24') opposite one another;

said anchor (13), which has a proximal end (51) and a distal end (52), wherein the proximal end (51) is arranged on the first end (24) of the first connector (20) and said fastener (18) is arranged on the second end (24') of the first connector (20);

said fastener (18) designed as a tube (25) in the form of a cylindrical sleeve (25'); and a second connector (27), wherein the second connector (27) has a strap (28), which has a free end (30) that is arranged to pivot in the tube (25), and said gripper (60) is arranged to pivot on the other end (54) of the pivotable second connector (27) along a longitudinal axis (33) in a longitudinal direction (53), and said gripper (60) has a leg spring (38), on which two spring arms (50, 50') that are parallel and separated by the leg spring (38) are arranged, and the two spring arms (50, 50') are connected to said leg spring (38).

22. The heart-valve-implant system according to claim 21, wherein the gripper (60) has a mouth part (56) that is formed by the spring arms (50, 50'), which mouth part is arranged resting on a fastening side (63) of the gripper (60) and on a side of the open leg spring (38) that faces away as well as on the longitudinal axis (33) of the tube (25), wherein the mouth part (56) has at least one spacer (88) that is arranged in the mouth part (56), which spacer creates a predetermined gap (89) between gears (87) of gripper jaws (86) in the mouth part (56).

* * * * *